United States Patent [19]

Goodrich, Jr. et al.

[11] Patent Number: 5,045,446

[45] Date of Patent: Sep. 3, 1991

[54] LYOPHILIZATION OF CELLS

[75] Inventors: Raymond P. Goodrich, Jr.; Christine M. Williams, both of Pasadena, Calif.

[73] Assignee: Cryopharm Corporation, Pasadena, Calif.

[21] Appl. No.: 378,349

[22] Filed: Jul. 11, 1989

Related U.S. Application Data

[63] Continuation-in-part of Ser. No. 237,583, Aug. 25, 1988, abandoned.

[51] Int. Cl.$^5$ .......................... A01N 1/02; C12N 5/08
[52] U.S. Cl. ...................................... 435/2; 424/533; 435/240.1
[58] Field of Search .................. 435/2, 240.1; 424/533

[56] References Cited

PUBLICATIONS

Scheiwe et al.-Chem. Abst. vol. 98 (1983), p. 14029b.
Fujirebio Inc.-Chem. Abst. vol. 102, (1985), p. 92530y.

Primary Examiner—Sam Rosen

[57] ABSTRACT

A process and medium are disclosed for the lyophilization of cells which comprises the use of solutions including monosaccharide hexoses and pentoses, and/or biocompatible amphipathic polymers to permit the reconstitution of viable cells.

18 Claims, No Drawings

LYOPHILIZATION OF CELLS

FIELD OF THE INVENTION

This is a continuation-in part of Ser. No. 237,583, filed Aug. 25, 1988, now abandoned. This invention relates to the general field of biochemistry and medical sciences, and specifically to processes for the preservation, storage and reconstitution of cells, particularly red blood cells.

BACKGROUND AND SUMMARY OF THE INVENTION

Laboratory cell preservation and storage have been significant problems for a variety of plant and animal cells. Freezing the cells in an aqueous solution and thawing the cells prior to use is not uncommon, but the viability of the cells after this process is generally severely affected and chromosome abnormalities often result from this freeze-thaw process. In addition, the expense of keeping the cells frozen is significant.

For example, there has been a need for improved methods for the storage of blood and blood constituents. Blood is a major tissue of the human body, and has as a predominant role the delivery of oxygen from the lungs to peripheral tissues. This role is carried out by erythrocytes, i.e., red blood cells (RBC). The oxygen is furnished from the lungs by an exchange-diffusion system brought about by a red, iron-containing protein called hemoglobin. When hemoglobin combines with oxygen, oxyhemoglobin is formed and after oxygen is given up to the tissues, the oxyhemoglobin is reduced to deoxyhemoglobin.

The red cell membrane is composed of two major structural units, the membrane bilayer and a cytoskeleton. A lipid bilayer and integral membrane proteins form the membrane bilayer, which has little structural strength and fragments readily by vesiculation. The other major component, the membrane skeleton, stabilizes the membrane bilayer and provides resistance to deformation. The cytoskeleton is linked to the bilayer in the erythrocyte membrane, possibly by lipid-protein as well as protein-protein associations. The hemoglobin, and other RBC components, are contained within the red cell membrane.

In adults, bone marrow is active in the formation of new red blood cells. Once erythrocytes enter the blood, these cells have an average lifetime of about 120 days. In an average person, about 0.83% of the erythrocytes are destroyed each day by phagocytosis, hemolysis or mechanical damage in the body, and the depleted cells are renewed from the bone marrow.

A wide variety of injuries and medical procedures require the transfusion of whole blood or a variety of blood components. Every patient does not require whole blood and, in fact, the presence of all of the blood components can cause medical problems. Separate blood fractions can be stored under those special conditions best suited to assure their biological activity at the time of transfusion. For example, when donor blood is received at a processing center, erythrocytes are separated and stored by various methods. Such cells are storable in citrate-phosphate-dextrose at 4° C. for up to five weeks, generally as a unit of packed erythrocytes having a volume of from 200 to 300 ml and a hematocrit value (expressed as corpuscular volume percent) of 70 to 90. Erythrocytes may also be treated with glycerol and then frozen at from $-30°$ to $-196°$ C. and stored for up to seven years in a glycerol solution, but must be kept frozen at low temperatures in order to survive sufficiently for transfusion. Both these methods require careful maintenance of storage temperature to avoid disruption of the desired biological activity of the erythrocytes, and provide a twenty-four hour survival time for at least 70% of the transfused cells, which is considered to be an acceptable level for use in transfusion practice in accordance with the American Association of Blood Bank standards.

It has thus been a desideratum to obtain a method for the storage of cells, and in particular red blood cells, which is not dependent on the maintenance of specific storage temperatures or other storage conditions. Such a method would facilitate the availability of erythrocytes for medical purposes and assist in the storage and shipment of various mammalian cells and plant cells, particularly protoplasts, for research and hybrid development.

One such desired method has been the lyophilization (freeze-drying) of cells, since such cells could be stored at room temperature for an extended period of time and easily reconstituted for use. Freeze-dried red blood cells could thus be easily stored for use in transfusions. However, prior to our invention, it has been impossible to freeze-dry erythrocytes in a manner which permits the reconstitution of the cells to form erythrocytes with an intact cytoskeleton and biologically-active hemoglobin, i.e., viable red blood cells. When RBCs have been lyophilized according to previous methods, for example in either an aqueous or phosphate-buffered saline (PBS) solution, the reconstituted cells are damaged to the extent that the cells are not capable of metabolizing, and the cell hemoglobin cannot carry oxygen. Glutaraldehyde-fixed erythrocytes, which have been lyophilized and reconstituted, have found use primarily in agglutination assays.

The process of the present invention allows for the lyophilization of cells under conditions which are not deleterious to the structure and the biological activity of the cell, and which permits the reconstitution of the lyophilized cells to form cells which are identical to the natural cells in a biological or botanical activity. Briefly, the process comprises immersing a plurality of cells in an essentially isotonic aqueous solution containing a carbohydrate, and which preferably includes an amphipathic polymer, freezing the solution, and drying the solution to yield freeze-dried cells which, when reconstituted, produce a significant percentage of intact and viable cells.

While the invention is applicable to a wide variety of plant and animal cells, the process of the invention is preferably applied to red blood cells and allows for the lyophilization of erythrocytes under conditions which maintain structure of the cell and the biological activity of the hemoglobin, and which permits the reconstitution of the lyophilized red blood cells to allow use on a therapeutic level. The carbohydrate of the invention is biologically compatible with the cells, that is, non-disruptive to the cells, and is preferably one which permeates, or is capable of permeating, the membrane of the cells. The carbohydrate may be selected from the group consisting of monosaccharides, since disaccharides do not appear to permeate the membrane to any significant extent. Monosaccharide pentoses and hexoses are preferred in concentrations of from about 7.0 to 37.5%, preferably about 23%. Xylose, glucose, ribose, mannose and fructose are employed to particular advantage. The lyophilization of RBCs in such a carbohydrate solution improves the recovery after lyophilization to at least 50% intact cells, as opposed to the fusing and destruction of the cell membrane during lyophilization in water solutions without the carbohydrate. Such reconstituted cells are only useful in producing ghost cells for agglutination assays or biochemical research, i.e., as model membrane systems. They are not viable cells capable of transporting oxygen or metabolizing.

As stated above, the addition to the carbohydrate solution of a water soluble, biologically compatible polymer adds significantly to the percentage of biologically-active hemoglobin which is retained in the cells and recovered after reconstitution of red blood cells after lyophilization. The polymer will preferably be amphipathic, meaning that there are hydrophilic and hydrophobic portions on a single molecule of the polymer. The polymer may be present in the solution in concentrations of from 0.7% up to saturation. Preferably, the polymer has a molecular weight in the range of from about 1K to about 360K, most preferably from about 5K to 80K, and most preferably to 50K, and is present in a concentration of from about 3.5% up to the limit of solubility of the polymer in the solution. Polymers selected from the group consisting of polyvinylpyrrolidone (PVP) and polyvinylpyrrolidone derivatives, and dextran and dextran derivatives provide significant advantages. Amino acid based polymers (i.e., proteins) or hydroxyethyl starch may also be employed. Other amphipathic polymers may be used, such as poloxamers in any of their various forms. The use of the carbohydrate-polymer solution in the lyophilization of red blood cells allows for the recovery of intact cells, a significant percentage of which contain biologically-active hemoglobin. While not intending to be bound by any theory, the amphipathic properties of the polymer allow them to bind to the cell membrane while protecting the membrane surface by extension of the hydrophilic portion into the aqueous environment. This may alleviate the damage to the cell membrane which causes other problems, such as cell aggregation. The use of the carbohydrate-polymer solution in the lyophilization of red blood cells allows for the recovery of intact cells, a significant percentage of which contain biologically-active hemoglobin.

As is shown by the data set forth below, the described solutions provide media which permit cells, particularly red blood cells, to be subjected to the stresses of freezing, water sublimation and reconstitution and to form freeze-dried cells which may be reconstituted to yield cells which are capable of functioning normally.

Unless indicated otherwise by the terminology or the context, all percentages set forth herein are expressed as weight percentages (i.e., weight of the solute versus the total weight of the solution).

DESCRIPTION OF THE PREFERRED EMBODIMENT

As noted above, the process of the invention provides a medium for the lyophilization and reconstitution of intact and biologically-active erythrocytes. While the media of the invention are novel it will be understood that apparatus and related techniques are known by those of skill in the art for the lyophilization of various materials, and biological samples in particular, and only the specific temperatures and apparatus employed in the examples are described herein. From this description, one of ordinary skill in the art will be capable of employing the media of the invention in a process for the freeze-drying and reconstitution of intact, viable red blood cells.

The term lyophilization is broadly defined as freezing a substance and then reducing the concentration of one of the solutes, namely water, by sublimation and desorption, to levels which will no longer support biological or chemical reactions. Usually, the drying step is accomplished in a high vacuum. However, with respect to the storage of cells and particularly erythrocytes, the extent of drying (the amount of residual moisture) is of critical importance in the ability of cells to withstand long-term storage at room temperature. In the method of the invention, cells may be lyophilized to a residual water content of less than 10%, preferably less than 5%, and most preferably to a water content of less than 3%.

EXAMPLE ONE

Packed red blood cells of variable blood type were obtained from a hospital blood donor center or drawn from healthy volunteers using heparin as an anticoagulant.

Repeated samples of these blood cells were washed with a phosphate buffered saline solution (10 mM mono- and di-basic sodium phosphate, 150 mM sodium chloride, 5 mM dextrose, and 10 mM adenosine at pH 7.2) three times with centrifugation at 14,000 rpm for 6 to 10 seconds to separate plasma and/or other cell types from the red blood cells.

Samples of these packed red blood cells were then suspended in a lyophilizing buffer containing 26.5% glucose in PBS solution at pH 7.2.

The suspension was then transferred to a flask which was subsequently immersed in liquid nitrogen ($-196°$ C.) until the sample was frozen. The flask was rotated evenly in the liquid nitrogen to assure even dispersion of solution on the walls of the flask.

The frozen samples were transferred to a bench top lyophilizer (Labconco model 4.5) operating at less than 100 microns of mercury vacuum with an inner chamber temperature of $-56°$ C. Samples were allowed to dry thoroughly (6–24 hours) until crystalline in appearance and brittle to touch and the flask was allowed to return to room temperature.

The samples were rehydrated at 37° C. using a solution containing 25.5% sucrose in a phosphate buffered saline solution. A volume of the rehydrating solution was added equivalent to the initial volume of the sample prior to drying.

It was found upon examination of the cells with an optical microscope that about 50% of the red blood cells had intact cell membranes. However, the hemoglobin was found not to be cell associated. Nonetheless, the hemoglobin in the solution was functional and if present in the cells would be effective as an oxygen carrier. Repeating this procedure with fructose and ribose solutions having concentrations of from about 7.0 to 37.5% produced nearly equal results, as did buffered solutions of xylose and mannose at concentrations of from about 7.0 to 37.5%.

Specifically, various monosaccharides were employed in the lyophilization of RBCs as described in this example, and the distribution of the hemoglobin in the recovered solution was noted. Oxyhemoglobin is capable of transporting oxygen to mammalian tissue. Methemoglobin is hemoglobin which cannot bind oxygen, but can possibly be reversed to form oxyhemoglobin when found in lower concentrations y the enzyme NADH methemoglobin reductase. Hemochrome is irreversibly degraded hemoglobin. In Table I, the recovery of greater than 90% oxyhemoglobin from cells lyophilized with solutions of ribose, mannose, fructose, xylose and glucose is shown.

TABLE I

| % Carbohydrate | % OxyHb | % MetHb | % Hemochrome |
|---|---|---|---|
| 23.1 Ribose | 93.1 | 5.4 | 1.5 |
| 26.5 Mannose | 94.2 | 6.0 | 0 |
| 26.5 Fructose | 98.0 | 1.3 | 0.7 |
| 26.5 Sorbose | 56.9 | 40.9 | 2.3 |
| 15.2 Galactose | 81.0 | 17.3 | 1.7 |
| 23.1 Xylose | 96.7 | 3.6 | 0 |
| 26.5 Glucose | 98.1 | 1.8 | 0.1 |

EXAMPLE TWO

A number od samples of packed red blood cells, obtained and washed as described in Example One, were suspended in a lyophilizing buffer containing 23.1% glucose and a concentration of either (a) 18% of 10K or (b) 12.8% of 40K polyvinylpyrrolidone in PBS at pH 7.2.

The suspension was then transferred to a flask which was subsequently immersed in liquid nitrogen ($-196°$ C.) until the sample was frozen. The flask was rotated evenly in the liquid nitrogen to assure even dispersion of solution on the walls of the flask.

The frozen sample was transferred to a bench top lyophilizer (Labconco model 4.5) operating at less than 100 microns of mercury vacuum with an inner chamber temperature of $-56°$ C. Samples were allowed to dry thoroughly (6-24 hours) until crystalline in appearance and brittle to touch and the flask was allowed to return to room temperature.

The samples were rehydrated at 37° C. using a solution containing 25.5% sucrose in a phosphate buffered saline solution. A volume of the rehydrating solution was added equivalent to the initial volume of the sample prior to drying.

The samples were centrifuged at 14,000 rpm in an Eppendorf microcentrifuge to pellet the rehydrated red blood cells in suspension.

The results of incorporating the polymer with the above described carbohydrate in the buffered lyophilizing solution produced surprising results not only in that the recovery of intact cells was maintained at $52.9 \pm 7.9\%$, but in addition the solution allowed hemoglobin retention by the cells of from 27.4 up to 42.2% for the 10K PVP and from 57.3 up to 65.5% for the 40K PVP, with greater than 80% of the hemoglobin being oxyhemoglobin. Further testing has shown that 24K PVP at a concentration of 12.8% and a glucose concentration of 23.1% produces even better results both in cell and hemoglobin recovery.

EXAMPLE THREE

The procedure described in Example Two was repeated, with different carbohydrates substituted for glucose in the lyophilizing buffer. Two different molecular weights of polyvinylpyrrolidone were used. The results are shown in Table II.

TABLE II

| PVP MW | % Carbohydrate | % Cell Recovery | % Hb Recovery |
|---|---|---|---|
| 10K* | 12.2 Galactose | 27.7 | 10.3 |
| | 21.7 Mannose | 57.6 | 30.6 |
| | 18.8 Xylose | 63.9 | 32.3 |
| | 21.7 Fructose | 54.6 | 28.1 |
| | 21.7 Glucose | 59.0 | 28.6 |
| 24K** | 13.0 Galactose | 26.3 | 13.8 |
| | 23.1 Mannose | 51.8 | 57.2 |
| | 20.0 Xylose | 48.4 | 55.9 |
| | 23.1 Fructose | 48.8 | 59.3 |
| | 23.1 Glucose | 59.0 | 52.7 |

*with a PVP concentration of from 18.1 to 20.3%
**with a PVP concentration of from 12.8 to 14.5%

Trehalose and sucrose in the lyophilizing solution showed marginal cell recovery, but no hemoglobin recovery.

EXAMPLE FOUR

The procedure described in Example Two (using from 21.7 to 26.3% glucose as the carbohydrate) was repeated substituting polyvinylpyrrolidone of different molecular weights and concentrations for those used in the lyophilizing buffer of the previously described Example. All other conditions were repeated as described in Example Two. The results are shown in Table III. The column headed MCHC refers to the mean cell hemoglobin content of the reconstituted cells. The MCHC of normal RBCs is $34 \pm 2$. Table III demonstrates that PVP may be employed with molecular weights of from 10 to 40K in concentrations of from 0.7 to 18.1%. The 40KT PVP had a viscosity of about 26 to 35 poise, and the 40K PVP had a viscosity of about 28 to 32 poise. Maltose showed no cell or hemoglobin recovery.

TABLE III

| PVP MW | Conc. (%) | % Hb Recovery | MCHC |
|---|---|---|---|
| 10K | 3.5 | 13.6 | — |
| | 6.8 | 15.0 | 34.9 |
| | 12.8 | $30.1 \pm 4.1$ (n = 3) | $20.9 \pm 3.1$ (n = 3) |
| | 18.1 | 36.5 | 28.1 |
| 24K | 3.5 | 24.7 | 17.3 |
| | 6.8 | 52.9 | 20.9 |
| | 12.8 | $52.7 \pm 6.3$ (n = 4) | $27.4 \pm 4.3$ (n = 4) |
| | 18.1 | $52.2 \pm 6.9$ (n = 2) | — |
| 40K | 3.5 | 17.7 | — |
| | 6.8 | 31.0 | 22.5 |
| | 12.8 | $61.4 \pm 4.1$ (n = 3) | $25.7 \pm 9.2$ (n = 3) |
| | 18.1 | $52.0 \pm 1.7$ (n = 2) | 37.4 |
| 40KT | 3.5 | 17.7 | — |
| | 6.8 | 31.8 | 25.0 |
| | 12.8 | $56.8 \pm 0.4$ (n = 2) | $36.3 \pm 2.8$ (n = 2) |
| | 18.1 | 50.0 | 29.4 |
| 360K | 0.7 | 9.4 | — |
| | 8.5 | 12.2 | — |

EXAMPLE FIVE

The experiment described in Example Two was repeated using polymers other than polyvinylpyrrolidone in the lyophilizing buffer. The results are summarized in Table IV.

TABLE IV

| Polymer | MW | % Conc. | % Hb Recovery |
|---|---|---|---|
| Dextran | 10K | 3.5 | 26.1 |
| | | 6.8 | 29.8 |
| | | 12.8 | 26.5 |
| | | 18.1 | 30.2 |
| | 40K | 3.5 | 24.7 |

TABLE IV-continued

| Polymer | MW | % Conc. | % Hb Recovery |
|---|---|---|---|
| | | 6.8 | 19.5 |
| | | 12.8 | 25.9 |
| | | 18.1 | 16.6 |
| | 80K | 3.5 | 15.2 |
| | | 6.8 | 26.5 |
| | | 12.8 | 20.2 |
| | | 18.1 | 18.7 |
| Ficoll | 70K | 3.5 | 17.3 |
| | | 6.8 | 19.1 |
| | 400K | 0.7 | 17.2 |
| | | 3.5 | 17.9 |
| Fish Gelatin | | 1.4 | 19.0 |
| | | 6.8 | 18.4 |
| Dextrin | | 1.4 | 20.4 |
| | | 6.8 | 13.1 |
| Albumin | | 1.4 | 29.7 |

EXAMPLE SIX

Samples of packed red blood cells were obtained and washed as described in Example One. These cells were suspended in a lyophilizing buffer of 12.8% 24K PVP and 23.1% glucose in phosphate buffered saline. The samples were lyophilized and reconstituted as described in Example Two, but with the various solutions used in the reconstitution of the cells. When water was the sole reconstituting liquid, the cells lysed within thirty minutes after reconstitution. An isotonic reconstituting solution, such as PBAS or PBSGA (PBS with the addition of 5 mmol glucose and 10 mmol adenosine) showed improvement, as did the use of reverse PBS, which employs potassium rather than sodium salts. Significant improvements were shown by the use of concentrations of up to 12.8% of either 10K or 24K PVP in the reconstitution solution.

The use of a carbohydrate in a minimum concentration of at least 0.7 to 3.6%, and most preferably at least 3.6%, provides better cell morphology after reconstitution. Both mono- and disaccharides may be employed for this purpose, although glucose, mannose, trehalose and sucrose are preferred with sucrose being the most preferred carbohydrate. These data are shown in Table V, wherein all carbohydrate and polymer solutions are formed in PBS.

TABLE V

| Solution | % Cell Recovery | % Hb Recovery | MCHC |
|---|---|---|---|
| Water | 49.3 ± 3.0 | 37.4 ± 1.1 | 29.9 ± 1.8 |
| PBS | 59.2 | 34.4 | 24.8 |
| PBSGA | 60.6 | 42.4 | 31.2 |
| Reverse PBS | 52.6 | 51.3 | 25.8 |
| Glucose 15.9% | 52.5 | 57.3 | 32.9 |
| Mannose 15.9% | 55.5 | 60.7 | 28.0 |
| Trehalose 27.4% | 65.7 | 59.4 | 24.9 |
| Sucrose | | | |
| 1.7% | 61.7 | 45.6 | 24.4 |
| 3.3% | 43.8 | 46.2 | 27.3 |
| 7.9% | 49.5 | 52.8 | 24.6 |
| 25.5% | 49.6 ± 10.6 | 51.4 ± 5.1 | 25.5 ± 2.1 |
| 4.8% 10K PVP | 55.6 ± 11 | 52.3 ± 3.0 | 23.5 ± 1.4 |
| 16.7% 10K PVP | 60.8 | 67.7 | 28.4 |
| 4.8% 24K PVP | 52.2 | 38.3 | 26.0 |
| 16.7% 24K PVP | 53.8 ± 9.4 | 73.1 ± 8.1 | 28.2 ± 8.7 |
| 3.6% 10K PVP + 24.6% Sucrose | 65.0 ± 6.5 | 59.0 ± 7.6 | 28.2 ± 8.7 |
| 13.0% 10K PVP + 22.2% Sucrose | 39.5 | 61.6 | 27.8 |
| 3.6% 24K PVP + 24.6% Sucrose | 64.8 | 59.3 ± 6.9 | 26.5 |
| 13.0% 24K PVP + | 77.7 | 76.4 ± 4.2 | 31.5 |

TABLE V-continued

| Solution | % Cell Recovery | % Hb Recovery | MCHC |
|---|---|---|---|
| 22.2% Sucrose | | | |

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein they are intended in a descriptive sense and not for purposes of limitation.

What is claimed is:

1. A process for the lyophilization of cells having a cell membrane, comprising immersing a plurality of cells in a water solution which includes a monosaccharide, which is capable of permeating the membrane of the cells, in a concentration of from about 7.0 to 37.5%; freezing the solution; and drying the frozen cells by sublimation of the water.

2. The process of claim 1 wherein the monosaccharide is selected from the group consisting of pentoses and hexoses.

3. The process of claim 1 or 2 wherein the monosaccharide is selected from the group consisting of xylose, glucose, ribose, mannose and fructose.

4. The process of claim 3 wherein the monosaccharide is present in the solution in a concentration of about 23%.

5. A process for the lyophilization of cells, comprising:
   immersing a plurality of cells in a buffered solution which includes:
   a monosaccharide which is present in the solution in a concentration of from about 7.0 to 37.5%, and
   a polymer having a molecular weight of from about 1K to about 360K which is present in a concentration of from about 0.7% up to saturation in the solution;
   freezing the solution; and
   drying the cells by sublimation of the water.

6. The process of claim 5 wherein said polymer is amphipathic.

7. The process of claim 5 wherein said polymer has a molecular weight in the range of about 5K to about 80K.

8. The process of claim 5, 6 or 7 wherein the monosaccharide is selected from the group consisting of pentoses and hexoses.

9. The process of claim 8 wherein the monosaccharide is selected from the group consisting of xylose, glucose, ribose, mannose and fructose.

10. The process of claim 8 wherein the polymer is selected from the group consisting of polyvinylpyrrolidone and dextran.

11. The process of claim 10 wherein the polymer is polyvinylpyrrolidone.

12. A process for the lyophilization of cells, comprising:
   immersing a plurality of cells in a buffered solution which includes:
   a monosaccharide which is present in the solution in a concentration of from about 7.0 to 37.5%, and
   a polymer having a molecular weight of from about 1K to about 360K which is present in a concentration of from about 0.7% up to saturation in the solution;

freezing the solution; and drying the cells by sublimation of the water.

13. The process of claim 12 wherein said polymer is amphipathic.

14. The process of claim 12 wherein said polymer has a molecular weight in the range of about 5K to about 80K.

15. The process of claim 12, 13 or 14 wherein the monosaccharide is selected from the group consisting of pentoses and hexoses.

16. The process of claim 15 wherein the monosaccharide is selected from the group consisting of xylose, glucose, ribose, mannose and fructose.

17. The process of claim 15 wherein the polymer is selected from the group consisting of polyvinylpyrrolidone and dextran.

18. The process of claim 17 wherein the polymer is polyvinylpyrrolidone.

* * * * *